(12) United States Patent
Hawkes

(10) Patent No.: US 8,056,720 B2
(45) Date of Patent: Nov. 15, 2011

(54) METHOD AND SYSTEM FOR MEDICAL INSTRUMENT STERILIZATION CONTAINERS

(75) Inventor: Jason Hawkes, Weare, NH (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 58 days.

(21) Appl. No.: 12/473,490

(22) Filed: May 28, 2009

(65) Prior Publication Data

US 2010/0300910 A1 Dec. 2, 2010

(51) Int. Cl.
*A61B 19/02* (2006.01)

(52) U.S. Cl. ............ 206/439; 206/363; 206/755

(58) Field of Classification Search .......... 206/439, 206/363, 370, 754, 755; 422/300
See application file for complete search history.

(56) References Cited

U.S. PATENT DOCUMENTS

| | | | | |
|---|---|---|---|---|
| 3,377,736 | A | * | 4/1968 | Woolworth .............. 43/57.1 |
| 3,966,408 | A | * | 6/1976 | Drennen et al. .......... 422/301 |
| 5,084,251 | A | | 1/1992 | Thomas |
| 5,284,632 | A | * | 2/1994 | Kudla et al. ............ 422/297 |
| 5,294,413 | A | * | 3/1994 | Riihimaki et al. ........ 422/297 |
| 5,346,677 | A | * | 9/1994 | Risk .................... 422/297 |
| 5,384,103 | A | * | 1/1995 | Miller ................... 422/310 |
| 5,424,048 | A | | 6/1995 | Riley |
| 5,540,901 | A | * | 7/1996 | Riley ................... 422/300 |
| 5,913,422 | A | | 6/1999 | Cote |
| 6,048,503 | A | * | 4/2000 | Riley et al. ............ 422/298 |
| D441,457 | S | * | 5/2001 | Neiner et al. ........... D24/217 |

* cited by examiner

*Primary Examiner* — J. Gregory Pickett
*Assistant Examiner* — King M Chu
(74) *Attorney, Agent, or Firm* — Hayes Soloway P.C.

(57) ABSTRACT

The system contains a base with a plurality of base ventilation holes and a plurality of side walls. The base includes a base instrument holder fixed to the base. At least one stage with a plurality of stage ventilation holes is positioned within the base. The stage includes at least two legs fixed to the stage, at least one stage instrument holder fixed to the stage, and a stage notched member fixed to the stage and positioned to engage a medical instrument beneath the stage. A fixed or removable cover having a plurality of cover ventilation holes is included to surround the base.

19 Claims, 7 Drawing Sheets

METHOD AND SYSTEM FOR MEDICAL INSTRUMENT STERILIZATION CONTAINERS

FIELD

The present disclosure is generally related to containers and more particularly is related to medical instrument sterilization containers.

BACKGROUND

Medical instruments are often held in sterilization trays prior to use, after use, and during sterilization. The instruments are laid out in the trays or placed on supporting members to insure that all areas of the instruments are sterilized. In order to maintain separation of the instruments in the tray, the instruments are supported or secured by brackets, clips, posts, and other devices attached to the tray. The separation of the instruments ensures that all areas of the instruments are properly sterilized and that damage to the instruments is minimized during transportation. However, for effective separation, only a few medical instruments may be placed in the tray at one time. The problem with current trays is that they are limited to the number of instruments that can be stored or sterilized in a single tray.

Thus, a heretofore unaddressed need exists in the industry to address the aforementioned deficiencies and inadequacies.

SUMMARY

Embodiments of the present disclosure provide a system and method for storing medical instruments. Briefly described, in architecture, one embodiment of the system, among others, can be implemented as follows. The system contains a base with a plurality of base ventilation holes and a plurality of side walls. The base includes a base instrument holder fixed to the base. At least one stage with a plurality of stage ventilation holes is positioned within the base. The stage includes at least two legs fixed to the stage, at least one stage instrument holder fixed to the stage, and a stage notched member fixed to the stage and positioned to engage a medical instrument beneath the stage. A cover having a plurality of cover ventilation holes is included to surround the base.

The present disclosure can also be viewed as providing methods for storing medical instruments. In this regard, one embodiment of such a method, among others, can be broadly summarized by the following steps: providing a base having at least one base instrument holder and a stage having at least one stage instrument holder and a stage notched member for securing medical instruments positioned below the stage; tilting the stage to expose the base instrument holder; inserting medical instruments into the base instrument holder and stage instrument holder; and lowering the stage to secure the medical instruments in the base instrument holder with the stage notched member.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the invention can be better understood with reference to the following drawings. The components in the drawings are not necessarily to scale. Instead emphasis is being placed upon illustrating clearly the principles of the present disclosure. Moreover, in the drawings, like reference numerals designate corresponding parts throughout the several views.

DETAILED DESCRIPTION

Figure 1:
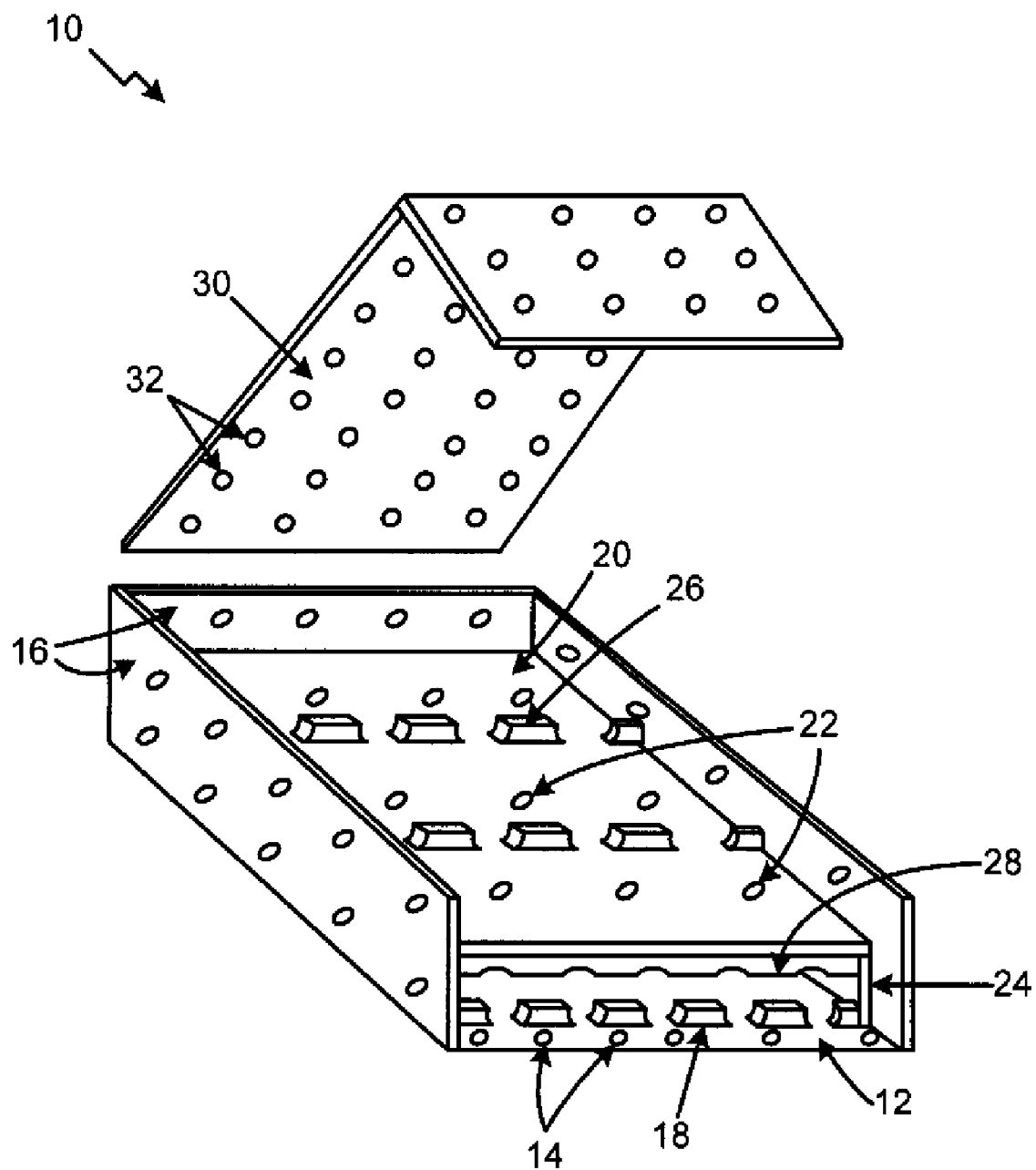
FIG. 1 is an illustration of a prospective view of a system for storing medical devices, in accordance with a first exemplary embodiment of the present disclosure.

Embodiments of the present disclosure provide a system and method for storing medical instruments. FIG. 1 is an illustration of a prospective view of a system 10 for storing medical devices, in accordance with a first exemplary embodiment of the present disclosure. The system contains a base 12 with a plurality of base ventilation holes 14 and a plurality of side walls 16. The base 12 includes a base instrument holder 18 fixed or removably fixed to the base 12. At least one stage 20 with a plurality of stage ventilation holes 22 is positioned within the base 12. The stage 20 includes at least one leg 24 fixed to the stage 20, at least one stage instrument holder 26 fixed to the stage 20, and a stage notched member 28 fixed to the stage 20 and positioned to engage a medical instrument beneath the stage 20. A cover 30 having a plurality of cover ventilation holes 32 is included to surround the base 12. As used herein, "fixed" may describe elements that are integrally formed, permanently attached and/or removably attached.

The system 10 may be a medical sterilization container. The base 12 may be constructed of aluminum, plastic or other material acceptable for use in a system 10 for holding and sterilizing medical instruments. The material of the base 12 should be durable when subject to frequent sterilization and transportation of the medical instruments. The base 12 includes a plurality of side walls 16 enclosing the base 12. The base 12 may be fully enclosed by the side walls on all sides of the base 12. As shown in FIG. 1, the base 12 may have one or more sides of the base 12 not having a side wall 16 to allow easier access to the inside of the base 12.

The base 12 further includes at least one base instrument holder 18 fixed to the base 12. The base instrument holder 18 can be any brackets, clips, posts, or combination of these or other devices fixed to the base 12 to secure medical instruments inside the base 12. The base instrument holder 18 is constructed of one or more materials that are durable when subject to sterilization and to storage of sharp medical instruments.

The base ventilation holes 14 may be of various shapes and sizes known to those having ordinary skill in the art to permit sterilization fluid or steam to reach the medical instruments inside the system 10. The base ventilation holes 14 are disposed on the surface of the base 12 and can also be included on the side walls 16 to ensure complete sterilization of the medical instruments.

The system 10 includes at least one stage 20 disposed within the base 12. The stage 20 allows for additional medical instruments to be supported inside the system 10 without the medical instruments on the stage 20 coming in contact with the medical instrument secured on the base 12 or other stages. The stage 20 may be made of the same materials as the base 12. The stage 20 includes stage ventilation holes 22 that may be the same shape and size as the base ventilation holes 14. The shape and size of the stage ventilation holes 22 may also be different from the base ventilation holes 14 in order to obtain more circulation of sterilization fluid throughout the system 10 when certain medical instruments require greater exposure to the sterilization fluid or steam.

The stage 20 includes at least one stage instrument holder 26 fixed to the stage 20 for supporting medical instruments. The stage instrument holder 26 may be any brackets, clips, posts, or combination of these or other devices attached to the tray 20 to secure the medical devices for sterilization, transportation, and storage.

The stage 20 also includes a stage notched member 28 fixed to the stage 20 to engage a medical instrument positioned below the stage 20. The stage notched member 28 engages the medical instrument below the stage 20 and allows the medical instrument to be firmly secured in the base instrument holders 18 so that the medical instruments do not slip out of the base instrument holder 18 during sterilization or transportation. The stage notched member 28 may be built in as part of the stage 20 having the notched sections in the shape needed to engage the medical instruments below the stage. The stage notched member 28 may also be a member attached to the bottom or side of the stage 20. The attached stage notched member 28 may include brackets, clips, posts, or combination of these or other devices to engage the medical devices positioned below the stage 20.

The stage 20 includes at least two legs 24 fixed to the stage 20 to support the stage 20 within the base 12. The legs 24 may be positioned on the base 12 to suspend the stage 20 above the base 12. The legs 24 or the sides of the stage 20 may also engage at least two of the side walls 16 in order to suspend the stage 20 above the base 12.

The system 10 further includes a cover 30 to surround the base 12. The cover 30 is shaped to enclose the base 12. FIG. 1 shows that when one side of the base 12 is not included, the cover 30 may be shaped to surround the exposed side of the base 12. The cover includes a plurality of cover ventilation holes 32 which may be various shapes and sizes known to those having ordinary skill in the art to permit sterilization fluid or steam to reach the medical instruments inside the system 10.

FIG. 1 shows the cover 30 being detachable from the base 12 and side walls 16. The cover 30 may engage the base 12 and side walls 16 to secure the cover 30 to the base 12 and side walls 16.

Figure 2:
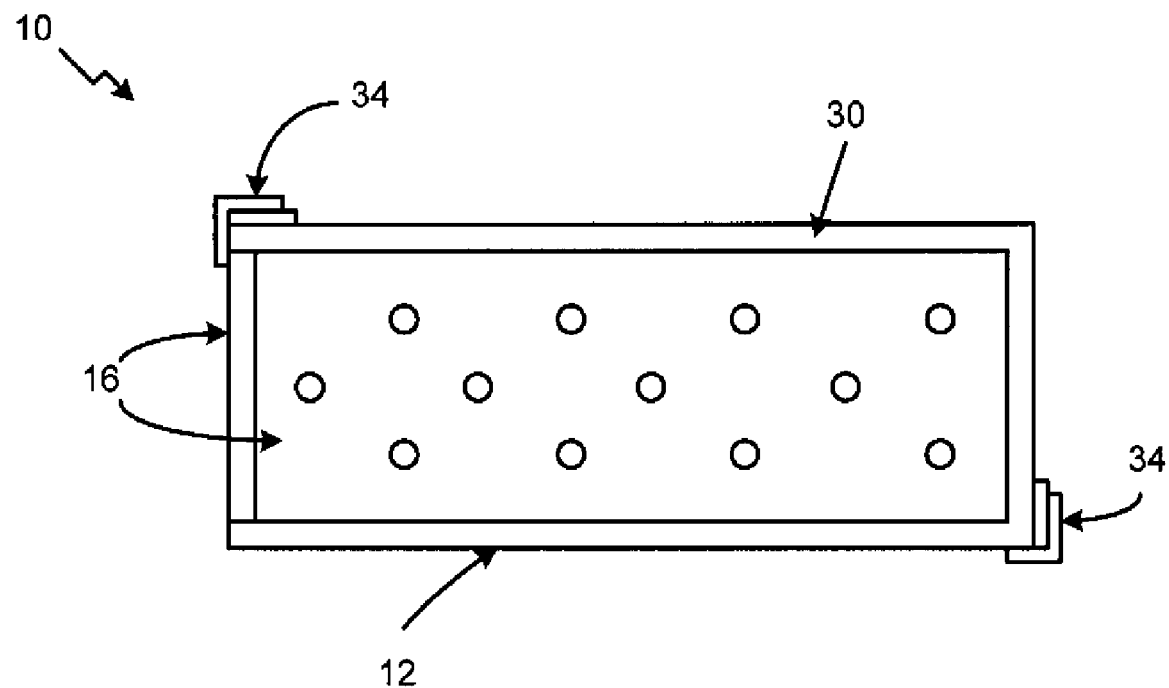
FIG. 2 is an illustration of the side view of the system of FIG. 1, in accordance with a first exemplary embodiment of the present disclosure.

FIG. 2 is an illustration of the side view of the system of FIG. 1, in accordance with a first exemplary embodiment of the present disclosure. FIG. 2 shows the system 10 having the cover 30 secured to the base 12 and side walls 16 with locking elements 34. The locking elements 34 may be latches or other locking elements known to those reasonably skilled in the art to be able to secure the cover 30 to the base 12 and side walls 16. The cover 30 may also have a pivotal connection with the base 12 or the side walls 16. The pivotal connection may be a removable pivotal connection. The pivotal connection may also have a locking mechanism to lock the cover 30 in a fixed position.

Figure 3:
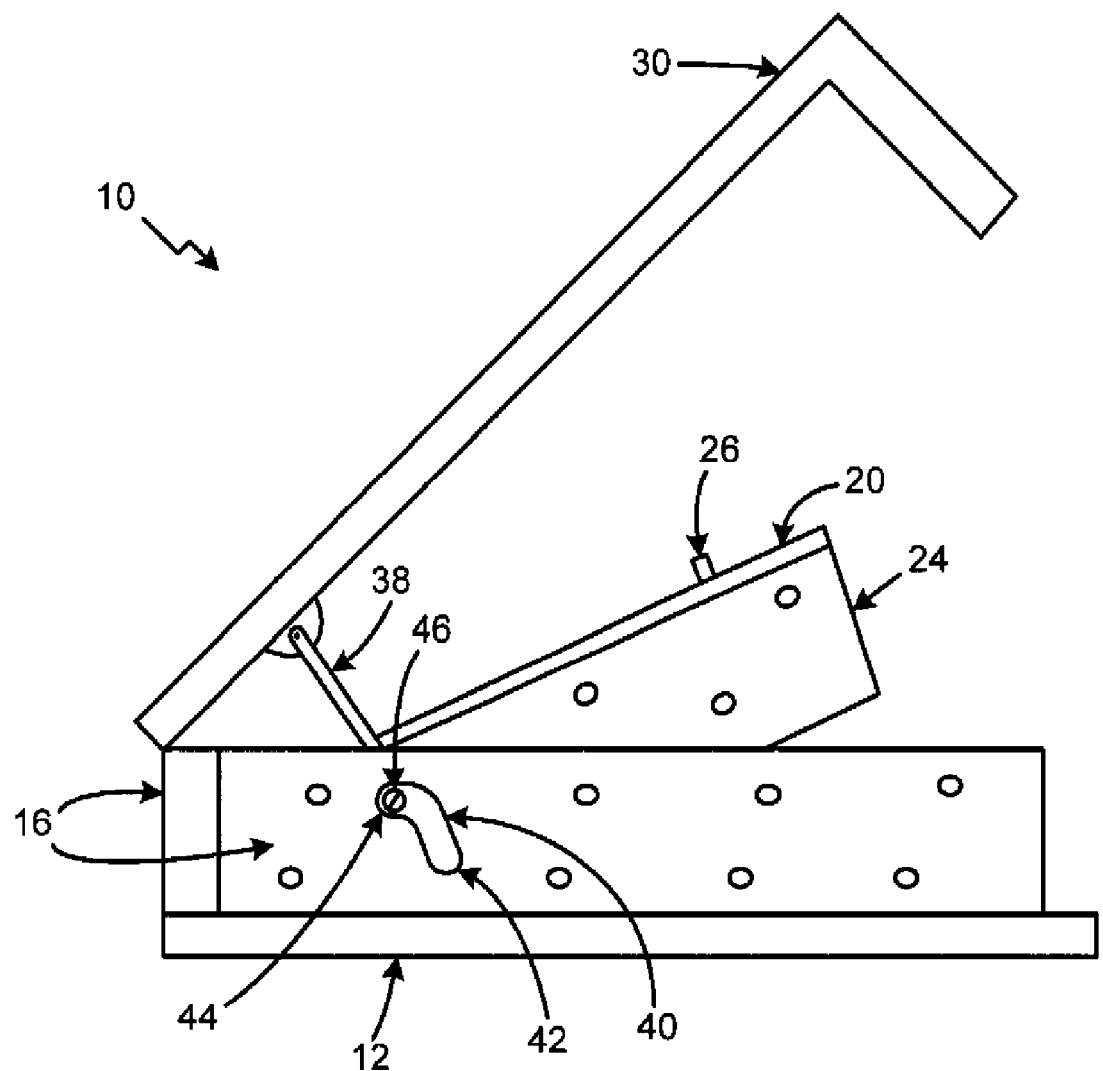
FIG. 3 is an illustration of a side view of the system of FIG. 1 with base elongated slots in the side walls, in accordance with a first exemplary embodiment of the present disclosure.

FIG. 3 is an illustration of a side view of the system 10 of FIG. 1 with base elongated slots 40 in the side walls 16, in accordance with a first exemplary embodiment of the present disclosure. The base elongated slots 40 have a lowered position 42 and a raised position 44. A pair of pins 46, or rollers, coupled to the stage 20, side walls 16, or the stage legs 24, engage the base elongated slots 40. The positioning of the pins 46, or rollers in the raised position 44 of the base elongated slots 40, tilts the stage 20 to expose the base instrument holder 18 (shown in FIG. 1) below the stage 20. The positioning of the pins 46, or rollers in the lowered position 42 on the base elongated slots 40, lowers the stage 20 and secures the medical instruments positioned below the stage 20. A pair of linking rods 38 may be included to link the cover 30 and the stage 20. Those having ordinary skill in the art will recognize other elements may be used in place of the pins or fillers to perform an equivalent function.

As shown in FIG. 3, the shape of the base elongated slot 40 may be varied to allow the stage 20 to lock in place when the pins 46 or rollers engage the raised position 44 of the base elongated slots 40. With the stage 20 tilted and locked in place the medical instruments can be loaded and unloaded from the base instrument holders 18 and stage instrument holder 26.

Figure 4:
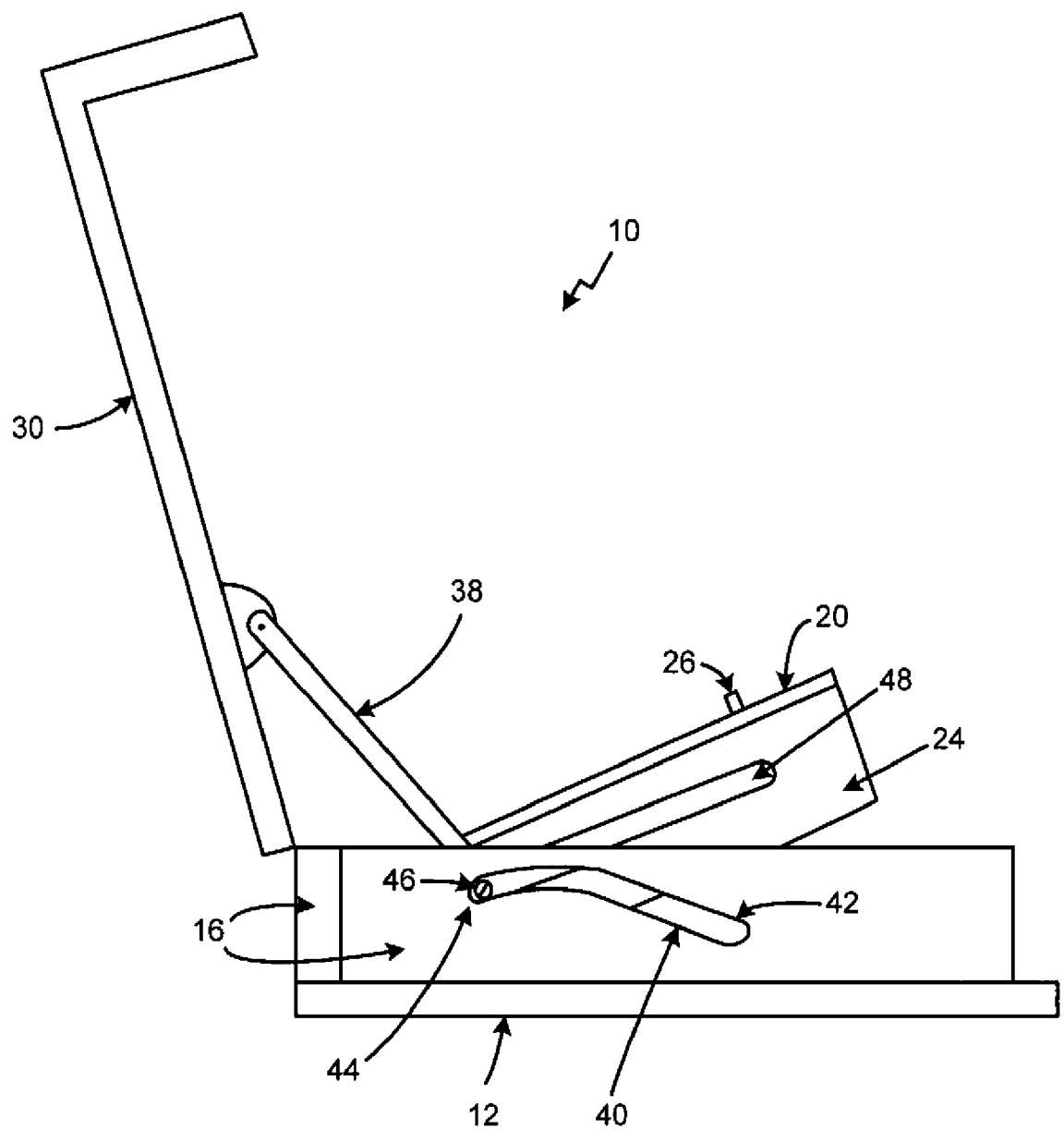
FIG. 4 is an illustration of a side view of the system of FIG. 4 with stage elongated slots in the stage legs, in accordance with a first exemplary embodiment of the present disclosure.

FIG. 4 is an illustration of a side view of the system of FIG. 3 with stage elongated slots 48 in the stage legs 24, in accordance with a first exemplary embodiment of the present disclosure. The stage 20 engages the side walls 16 of the base 12 by pins 46 sliding along the stage elongated slots 48 and the base elongated slots 40. The base elongated slots 40, stage elongated slots 48, and the pins 46 or rollers allow for the stage 20 to slidably engage the side walls 16 as the stage 20 is tilted.

This embodiment may also include a pair of linking rods 38, shown in FIG. 3 and FIG. 4, connected to the cover 30 on one end and to the pins 46 or stage 20 on the other end. When the cover 30 is in the closed position the pins 46 are positioned in the lowered position 42 of the base elongated slots 40. The opening of the cover 30 slides the pins 46 from the lowered position 42 on the base elongated slots 40 to the raised position 44 on the base elongated slots 40. The sliding of the pins from the lowered position 42 to the raised position 44 tilts the stage 20 exposing the base instrument holder 18 (shown in FIG. 1) below the stage 20. When the cover 30 is closed the pins 46 slide into the lowered position 42 on the base elongated slots 40, lowering the stage 20 and securing any medical instruments positioned below in the base instrument holder 18.

As shown in FIG. 4, using the stage elongated slot 48 with the first exemplary embodiment can also allow for the base elongated slot 40 to be shaped to allow the cover 30 and the stage 20 to lock in place when the pins 46 engage the raised position 44 of the base elongated slot 40. In the raised position 44 the pins lock the cover 30 and the stage 20 in a tilted position exposing the base instrument holder 18 (shown in FIG. 1) below the stage 20. The tilted stage 20 allows the instruments to be loaded and unloaded from the base instrument holder 18.

Figure 5:
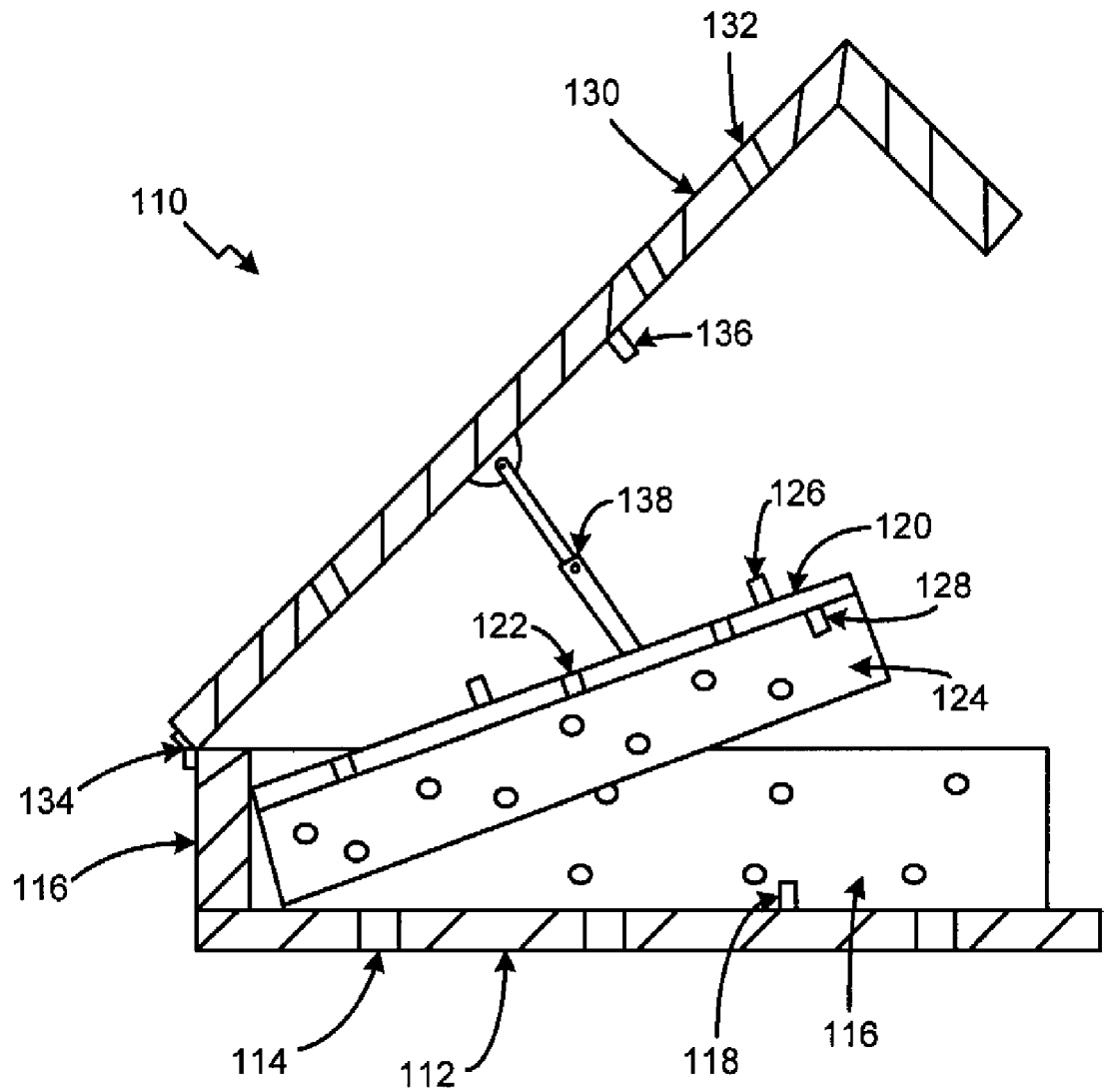
FIG. 5 is a side view of the system, in accordance with a second exemplary embodiment of the present disclosure.

FIG. 5 is a side view of the system 110 in accordance with a second exemplary embodiment of the present disclosure. The system contains a base 112 with a plurality of base ventilation holes 114 and a plurality of side walls 116. The base 112 includes a base instrument holder 118 fixed to the base 112. At least one stage 120 with a plurality of stage ventilation holes 122 is positioned within the base 112. The stage 120 may include at least one leg 124 secured to the stage 120 or base 112, at least one stage instrument holder 126 fixed to the stage 120, and a stage notched member 128 fixed to the stage 120 and positioned to engage a medical instrument beneath the stage 120. A cover 130 having a plurality of cover ventilation holes 132 is included to surround the base 112. The cover 130 is pivotally connected to the base 112 or at least one of the side walls 116.

The pivotal connection allows the cover 130 to be movable between a closed position and an opened position. The pivotal connection 134 may include a hinged connection. The pivotal connection 134 may also include the use of hinge pins, but hinges, or other type of connections known to those having ordinary skill in the art to permit the cover 130 to pivotally connect to the side walls 116. The pivotal connection 134 may be a removable pivotal connection to allow the cover 130 to be removed from the base 112.

The cover 130 may also include at least one cover notched member 136 to secure at least one medical instrument positioned on the stage 120. The cover notched member 136 allows the medical instruments on the stage 120 to be firmly secured in the stage instrument holder 126 during sterilization, storage, or transportation. The cover notched member 136 may be part of the cover 130 having the notched sections in the shape needed to secure the medical instruments on the stage 120. The cover notched member 136 may also be a member attached to the bottom of the cover 130. The attached cover notched member 136 may include brackets, clips, posts, or combination of these or other devices to secure the medical devices positioned below the cover 130.

In accordance with the second exemplary embodiment, the system 110 may include a pair of linking rods 138 secured to the cover 130 on one end and to the legs of the stage on the other, to tilt the stage 120. As shown in FIG. 3, the pair of linking rods 138 tilt the stage 120 when the cover 130 is in the open position. When the cover 130 is in a closed position the linking rods 138 lower the stage 120 securing any medical instrument below the stage 120 with the stage notched member 128. The tilting of the stage 120 provides access to the base 112 or additional stages below the tilting stage 120. Having the cover 130 open and the stage 120 tilted, medical instruments can be easily loaded or unloaded from the stage instrument holder 126 and base instrument holder 118.

The system of the second exemplary embodiment, shown in FIG. 5 may include a locking mechanism to lock the cover 130 into place when the cover 130 is opened. The locking mechanism may be part of the pivotal connection 134 implementing a locking hinge or part of the linking rods 138. The locking mechanism allows for the cover 130 to remain open, leaving the stage 120 tilted and locked in place while the medical instruments are loaded and unloaded from the base stage instrument holder 118 and stage instrument holder 126. When the cover 130 is closed the stage 120 is lowered, securing any medical instruments with the stage notched member 128 positioned below the stage 120.

Figure 6:
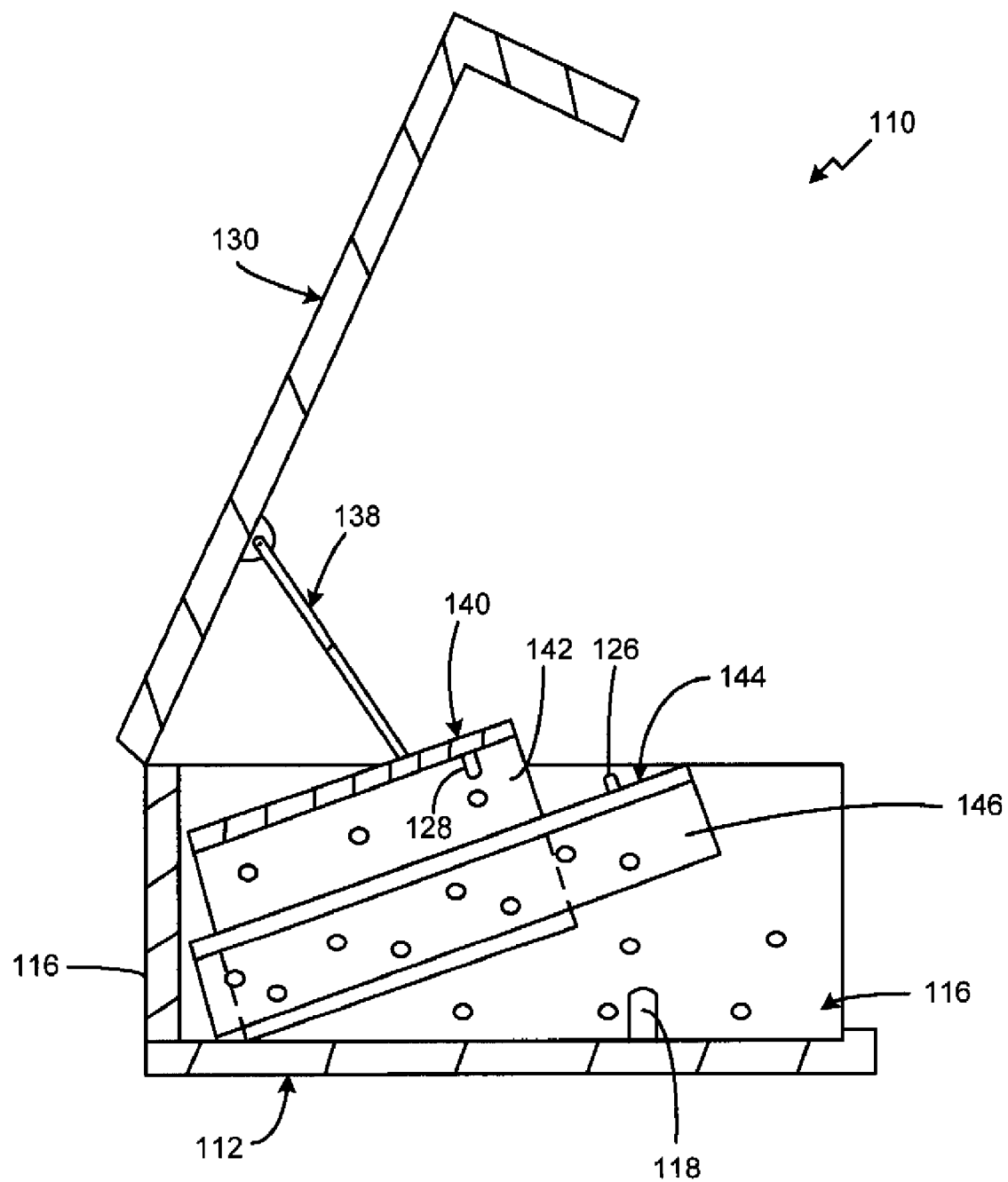
FIG. 6 is a side view of the system, in accordance with a second exemplary embodiment of the present disclosure having multiple stages.

FIG. 6 is a side view of the system, in accordance with a second exemplary embodiment of the present disclosure having multiple stages 120. The system may include a top stage 140 having top stage legs 142 and a bottom stage 144 having bottom stage legs 146. The top stage 140 and bottom stage 144 may engage the side walls 116 or they may be disposed on the base 112. FIG. 6 shows the stages positioned one above the other but the system may also include multiple stages positioned next to each other or in a combination of multiple stages where some are positioned on top of other stages and others are positioned next to other stages. Varying the positioning of multiple stages allows for the system to be adapted to the particular medical instruments that need to be steadied. In the system of the second exemplary embodiment having multiple stages, the stages 140 and 144 can be coupled or linked together allowing all of the stages 140 and 144 to tilt when the top stage 140 is tilted. The top stage 140 and bottom stage 144 may be coupled by rivets, bolts, pins or other means known by those reasonably skilled in the art of the present disclosure. The stages may be coupled to allow the top stage 140 and bottom stage 144 to tilt at different angles.

The tilting of the stages 140 and 144 releases the medical instruments secured by the stage notched member 128 on each stage and allows the medical instruments to be loaded and unloaded from the base instrument holders 118 and stage instrument holders 126. The top stage 140 may include a pair of linking rods 138 connected to the cover 130 on one end and to the top stage 140 on the other. As the cover 130 is raised, the top stage 140 tilts together with the bottom stage 144, possibly at varying angles, when the stages are coupled together. The linking rods 138 may also be provided for each stage 140 and 144 to tilt each of the stages 140 and 144 by separate set of linking rods 138.

As shown in FIG. 6 the top stage legs 142 and bottom stage legs 146 may extend to the base 112 when the stages 140 and 144 are lowered. This allows for the legs of the stages to sit on the base 112 and does not require that the side walls 116 of the base 112 support or engage the stage legs 142, 146. The top stage legs 142 and bottom stage legs 146 may also be adjusted to ensure that enough space if provided for medical instruments to be placed between the stages and the base 112. The top stage legs 142 may also be positioned on top of the bottom stage 144.

Figure 7:
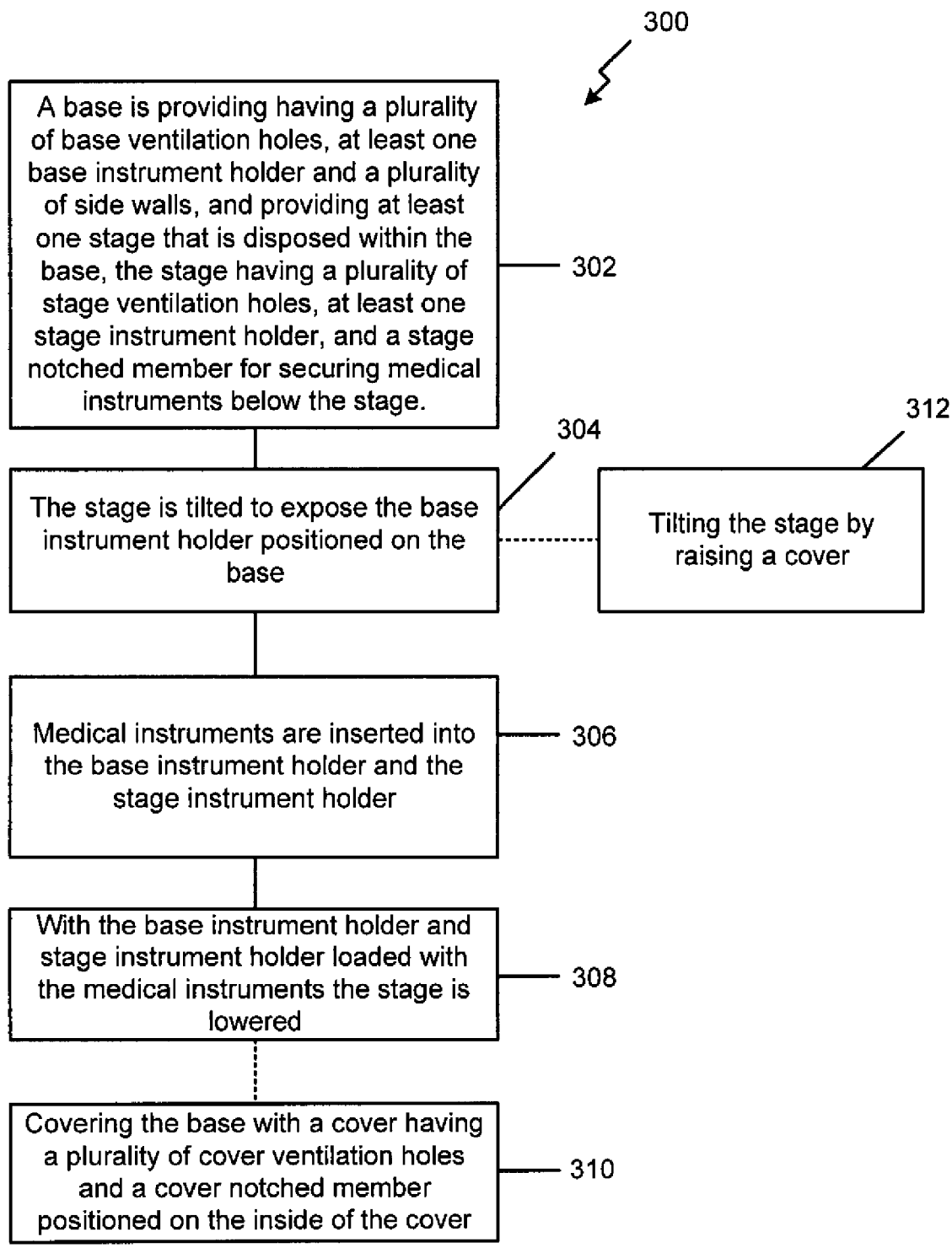
FIG. 7 is a flowchart illustrating a method of using the system of FIG. 1 to store medical instruments, in accordance with the first exemplary embodiment of the present disclosure.

FIG. 7 is a flowchart 300 illustrating a method of using the system 10 of FIG. 1 to store medical instruments, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 302, a base 10 is provided having a plurality of base ventilation holes 14, at least one base instrument holder 18 and a plurality of side walls 16. The step also includes providing at least one stage 20 that is disposed within the base 12, the stage 20 having a plurality of stage ventilation holes 22, at least one stage instrument holder 26 and a stage notched member 28 for securing medical instruments below the stage 20. The stage 20 is tilted to expose the base instrument holder 18 positioned on the base 12 (block 304). The tilting of the stage 20 may include the tilting of multiple stages 20 coupled to tilt together. Medical instruments are inserted into the base instrument holder 18 and the stage instrument holder 26 (block 306). With the base instrument holder 18 and stage instrument holder 26 loaded with the medical instruments, the stage 20 is lowered (block 308). Lowering the stage 20 secures the medical instruments positioned below the stage 20 with the stage notched member 28.

In accordance with the second embodiment shown in FIG. 3, the method may further include the step of covering the base 112 with a cover 130 having a plurality of cover ventilation holes 132 and a cover notched member 136 positioned on the inside of the cover 130 (block 310). As the cover 130 is closed the cover notched member 136 engages a medical instrument positioned in the stage instrument holder 126.

The step of tilting the stage 120 (block 304) may further comprise the step of raising a cover 130 (block 312) having the plurality of cover ventilation holes 132. The cover 130 is coupled to the stage 120 with a pair of linking rods 138 secured to the cover 130 on one end and to the stage 120 on the other. The linking rods 138 tilt the stage 120 when the cover 130 is raised. The tilting of the stage 120 exposes the base instrument holder 118 positioned below the stage 120.

It should be emphasized that the above-described embodiments of the present disclosure, particularly, any "preferred" embodiments, are merely possible examples of implementations, merely set forth for a clear understanding of the principles of the disclosed system and method. Many variations and modifications may be made to the above-described embodiments of the disclosure without departing substantially from the spirit and principles of the disclosure. All such modifications and variations are intended to be included herein within the scope of this disclosure and protected by the following claims.

What is claimed is:

1. A system for storing medical instruments, comprising:
a base having a plurality of base ventilation holes, a plurality of side walls, and at least one base instrument holder fixed to the base;
at least one stage disposed within the base, having a plurality of stage ventilation holes, at least one stage instrument holder fixed to the stage, at least one leg fixed to the stage, and a stage notched member fixed to the stage and positioned to engage a medical instrument beneath the stage, wherein the stage is movably linked to the base with at least two pivotal connections, wherein a first of the at least two pivotal connections is positioned on a first side wall of the stage and a second of the at least two pivotal connections is positioned on a second side wall of the stage, wherein the first side wall of the stage is positioned opposite the second side wall of the stage, wherein the at least two pivotal connections further comprise elongated slots having a lowered position and a raised position, wherein a pair of pins coupled to the stage engage the base elongated slots to tilt the stage, thereby exposing the base instrument holder below the stage when the pins engage the raised position of the base elongated slot; and
a cover having a plurality of cover ventilation holes, the cover engaging the base.

2. The system of claim 1, wherein a leg of the stage engages at least one of the side walls of the base.

3. The system of claim 1, wherein the cover further comprises a latch to secure the cover to the base.

4. A system for storing medical instruments, comprising:
a base having a plurality of base ventilation holes, a plurality of side walls, and at least one base instrument holder fixed to the base;
at least one stage disposed within the base, having a plurality of stage ventilation holes, at least one stage instrument holder fixed to the stage, at least one leg fixed to the stage, and a stage notched member fixed to the stage and positioned to engage a medical instrument beneath the stage; and
a cover having a plurality of cover ventilation holes, the cover engaging the base, wherein two of the side walls have base elongated slots having a lowered position and a raised position, wherein a pair of pins coupled to the stage engage the base elongated slots to tilt the stage, thereby exposing the base instrument holder below the stage when the pins engage the raised position of the base elongated slot.

5. The system of claim 4, further comprises a pair of linking rods secured between the cover on one end and to the pins on another end, to position the pins in the raised position on the base elongated slots and tilt the stage when the cover is opened.

6. The system of claim 4, wherein the cover and the stage lock into place when the pins are positioned in the raised position on the base elongated slots.

7. The system of claim 4, wherein each stage leg has a stage elongated slot for the pins to travel along, whereby the stage slidably engages with the side walls when tilting the stage.

8. The system of claim 7, further comprising a pair of linking rods secured between the cover on one end and to the pins on another end, to position the pins in the raised position on the base elongated slots and tilt the stage when the cover is opened.

9. The system of claim 7, wherein the cover and the stage lock into place when the pins are positioned in the raised position on the base elongated slots.

10. The system of claim 1, wherein the cover is pivotably connected to at least one of the side walls of the base.

11. The system of claim 1, wherein the cover includes a cover notched member positioned to engage a medical instrument in the stage instrument holder.

12. The system of claim 1, further comprising a pair of linking rods secured between the cover on one end and to at least one stage on another end, thereby tilting the stage, exposing the base instrument holder, when the cover is opened.

13. The system of claim 12, further comprising a locking mechanism to lock the cover and the stage into place when the cover is opened.

14. The system of claim 1, wherein the at least one stage further comprises plurality of stages.

15. The system of claim 14, wherein the multiple stages are coupled to tilt cooperatively.

16. A method for storing medical instruments, the method comprising the steps of:
providing a base having a plurality of base ventilation holes, at least one base instrument holder and a plurality of side walls, wherein two of the side walls have base elongated slots having a lowered position and a raised position, and at least one stage disposed within the base, the stage having a plurality of stage ventilation holes, at least one stage instrument holder fixed to the stage, and a stage notched member fixed to the stage and positioned to engage a medical instrument beneath the stage;
engaging the based elongated slots with a pair of pins coupled to the stage to tilt the stage;
exposing the base instrument holder below the stage when the pins engage the raised position of the base elongated slot;
inserting at least one medical instrument into the base instrument holder; and
lowering the stage to secure the medical instrument in the base instrument holder with the stage notched member.

17. The method of claim 16, further comprising covering the base with a cover having a plurality of cover ventilation holes and a cover notched member for securing the medical instruments in the stage instrument holder.

18. The method of claim 16, wherein the step of exposing the base instrument holder further comprises the step of raising a cover having a plurality of cover ventilation holes, wherein the cover is coupled to the stage tilting the stage when the cover is raised.

19. The method of claim 16, wherein the step of exposing the base instrument holder further comprises tilting multiple stages coupled to tilt together.

* * * * *